Figure 1:
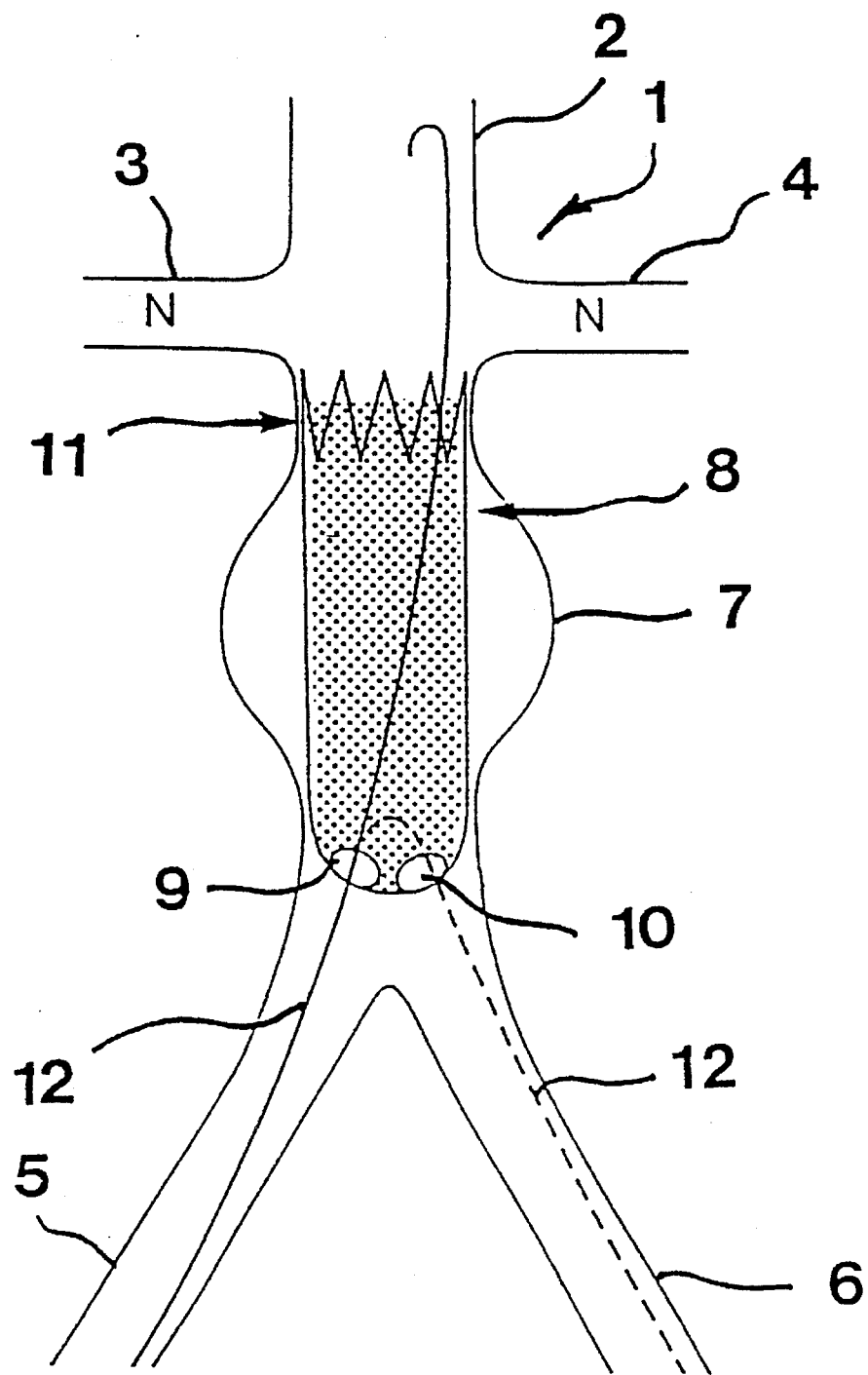

United States Patent [19]

Vorwerk et al.

[11] Patent Number: 5,562,724
[45] Date of Patent: Oct. 8, 1996

[54] ENDOVASCULAR GRAFT PROSTHESIS AND AN IMPLANTATION METHOD FOR SUCH A PROSTHESIS

[75] Inventors: Dierk Vorwerk; Rolf W. Günther; Thomas Schmitz-Rode, all of Aachen, Germany

[73] Assignee: William Cook Europe A/S, Bjaeverskov, Denmark

[21] Appl. No.: 446,761

[22] PCT Filed: Dec. 15, 1994

[86] PCT No.: PCT/DK94/00468

§ 371 Date: Jun. 2, 1995

§ 102(e) Date: Jun. 2, 1995

[87] PCT Pub. No.: WO95/16406

PCT Pub. Date: Jun. 22, 1995

[30] Foreign Application Priority Data

Dec. 15, 1993 [DE] Germany .................... 9319267 U

[51] Int. Cl.⁶ ..................................................... A61F 2/06
[52] U.S. Cl. ................... 623/1; 623/12; 606/195; 606/198
[58] Field of Search ................. 623/1, 11, 12; 606/108, 191, 194, 195, 198; 604/96, 104, 281

[56] References Cited

FOREIGN PATENT DOCUMENTS

| 0461791 | 12/1991 | European Pat. Off. . |
| 0508473 | 4/1992 | European Pat. Off. . |
| 0539237 | 4/1993 | European Pat. Off. . |
| 0551179 | 7/1993 | European Pat. Off. . |

*Primary Examiner*—Randy C. Shay
*Attorney, Agent, or Firm*—Richard J. Godlewski

[57] ABSTRACT

An endovascular graft prosthesis for arrangement at or in the vicinity of a bifurcation in the arterial system of a patient, e.g. for the purpose of repairing an aneurysm or the aortic bifurcation comprises a substantially tubular main body for location in the principal upstream arteria above the bifurcation such as th aorta and substantially tubular legs joining said main body in a bifurcation and extending into each of two branch arteries such as the iliac arteries. The main body (8) is substantially bag-shaped with an open proximal upstream end and a distal downstream bottom region in which two outlet openings (9, 10) are provided and is attachable to the inner side of the principal arteria (2) by means of an expandable stent device (11). The legs are made as separate expandable leg stent devices (15, 16) which may be introduced in a collapsed condition through the branch arteries and into the outlet openings (9,10) of the main body by means of guide wires (13,14) to engage against the rim of the corresponding outlet opening to provide a leakage-free bifurcated graft prosthesis.

11 Claims, 3 Drawing Sheets

ENDOVASCULAR GRAFT PROSTHESIS AND AN IMPLANTATION METHOD FOR SUCH A PROSTHESIS

The invention relates to an endovascular graft prosthesis for arrangement at or in the vicinity of a bifurcation in the arterial system of a patient and comprising a substantially tubular main body for location in an upstream arteria above the bifurcation and substantially tubular legs joining said main body and extending via the bifurcation into each of two downstream branch arteries, said main body being made of a flexible microporous and surgically implantable woven material unpenetratable to blood.

In particular, the invention is concerned with the repair of an aneurysm in the vicinity of the aortic bifurcation, but it may also be applied to other parts of the arterial system where a principal upstream arteria bifurcates into two branch arteries.

In order to prevent an aortic aneurysm, in particular in the lower part of the aorta close to the aortic bifurcation from causing a dangerous rupture of the aortic wall it is known to deploy a graft prosthesis in the region of the vessel affected by such an aneurysm.

An aortic aneurysm may develop as a result of a reduction of the strength of the aortic wall whereby the diameter of the affected part of the aorta may increase to more than 5 cm. Such expansions may result in flow irregularities and promotion of deposits of coagulated blood in the affected region. At increased expansion the remaining strength of the aortic wall will naturally decrease and may ultimately result in rupture of the vessel with an inherent danger of acute bleeding.

With conventional prior art endovascular prosthesis for aortic implantation surgical opening of the actual vascular section will be necessary for deployment of the prosthesis. For this purpose a partial cut is made in the wall of the aneurysm to introduce the prosthesis formed as an integral unit of a plastic material and secure it by sewing.

From EP-A-0508473 and EP-A-0539237 bifurcated graft prosthesis are known which may be transluminarly implanted for the repair of an aneurysm at or in the vicinity of the aortic bifurcation. In both cases the bifurcated prosthesis is made as an integral unit with a main body and two tubular legs joining the main body in a bifurcation. Due to this design the implantation operation becomes relatively complicated since the integral unit must be introduced through one of the iliac arteries with one of the legs in a fold-over condition until the graft is disposed proximal of the aortic bifurcation following which the proximal extremity of the prosthesis must be secured upstream of the actual vascular section and the folded overleg must be pulled down into the other iliac arteria.

It is the object of the invention to provide an endovascular graft prosthesis of the kind set forth for transluminal implantation at the aortic bifurcation by a considerably simpler implantation operation than the above-mentioned prior art solutions.

In order to achieve this an endovascular graft prosthesis according to the invention is characterized in that the main body is substantially bag-shaped with an open proximal upstream end and a distal downstream bottom region in which two outlet openings are provided, said main body being radially expandable and attachable in a radially expanded condition to the inner side of said upstream arteria upstream of the bifurcation by fixation means, said legs being made as separate resilient and radially expandable leg stent devices adapted for introduction in a collapsed condition through said branch arteries and into said outlet openings, each of said stent devices being engageable in its radially expanded condition against the rim of the corresponding outlet opening to provide a leakage-free bifurcated graft prosthesis.

By making up the prosthesis from a number of separate components which may be sequentially introduced in the arterial system by percutaneous operations through small openings with a punctual diameter up to 5 mm the components may be endovascularly assembled to a complete prosthesis after deployment in the actual vascular section. Thereby, the prosthesis according to the invention may also be applied for repair of an aneurysm extending into the iliac arteries.

The invention further relates to a method for implanting an endovascular graft prosthesis for deployment at or in the vicinity, a bifurcation in the arterial system of a patient and associated branch arteries.

According to the invention this method is characterized by the steps of introducing through a first branch arteria in an upstream direction by means of a first guide wire a separate, radially expandable and substantially bag shaped main body into an upstream arteria to extend into a region thereof above the bifurcation, said main body having an open proximal upstream end with associated fixation means and a distal downstream bottom region in which two outlet openings are provided, expanding said main body radially in said upstream arteria with said proximal end attached to the wall thereof, and introducing by means of said further guide wires a radially expandable leg stent device through each of the branch arteries into each of said outlet openings.

By this method the main body consisting of a micro porous woven material unpenetratable to blood may be guided by means of a guide wire from a puncture in an iliac arteria into the aorta and deployed there with a downstream orientation of the distal bottom region of the body with respect to the blood flow direction. Thereby, the guide wire will be coaxially located in one or both of the outlet openings of the bag-shaped body. In spite of the two outlet openings the main body will be sufficiently expanded by the blood flow in its bottom region. In this condition, the main body is secured to the inner wall of the aorta upstream of the bifurcation by means of a radially expandable stent device which may typically be a self-expandable metallic stent. Following subsequent introduction of guide wires through the two outlet openings and across the lumen of the stent device a leg stent device may be introduced over each guide wire to extend at least through the distance between the bottom region of the main body and the junction of the iliac arteries. The leg stent devices forming separate components of the prosthesis may have an elastic covering over their entire length and are also radially expandable.

The introduction of the two leg stent devices which may also be self-expandable metallic stents may take place by use of conventional catheter technique whereby the guide wire and the catheter are guided from one outlet opening through the other and into the opposite iliac arteria from where it may be guided in a conventional way through the vessel to the skin. By drawing of the curved guide wire extending through the outlet openings the position of the main body may still be corrected. Subsequently, two catheters may be introduced into the outlet openings over the guide wire thus positioned from the two groins to allow coaxial introduction of two guide wires to replace the two catheters. Subsequently the two leg stents covered by woven material are introduced over the positioned guide wires which can take place simultaneously for both stent devices.

In the expanded condition the two leg stents will press against the rim of the outlet openings and complete the main body into a leakage free endovascular prosthesis with a bifurcation secured in the aorta.

Preferably the main stent is attached to the bag-shaped main body with the downstream distal end overlapped by the upstream proximal end of the main body.

By a further development of the invention the endovascular deployment of the prosthesis may be substantially facilitated if the main stent device and the leg stent devices in a manner known per se are formed by self-expandable metal stents.

According to a further embodiment of the invention the rim of each outlet opening may diverge in the downstream direction.

By this measure there will be formed in each outlet opening close to the inner side of the bottom region of the bag-shaped main body a radially inwardly projecting opening rim against which the external side of the leg stent may engage tightly whereby the security against leakage will be increased.

Further, according to an embodiment of the invention the maximum external diameter of each of the leg stents may be 2–4 mm greater than the minimum rim diameter of each outlet opening.

Thereby, the components may be connected in a sufficiently stable and leakage free manner without any requirement for additional means for this purpose.

Figure 2:
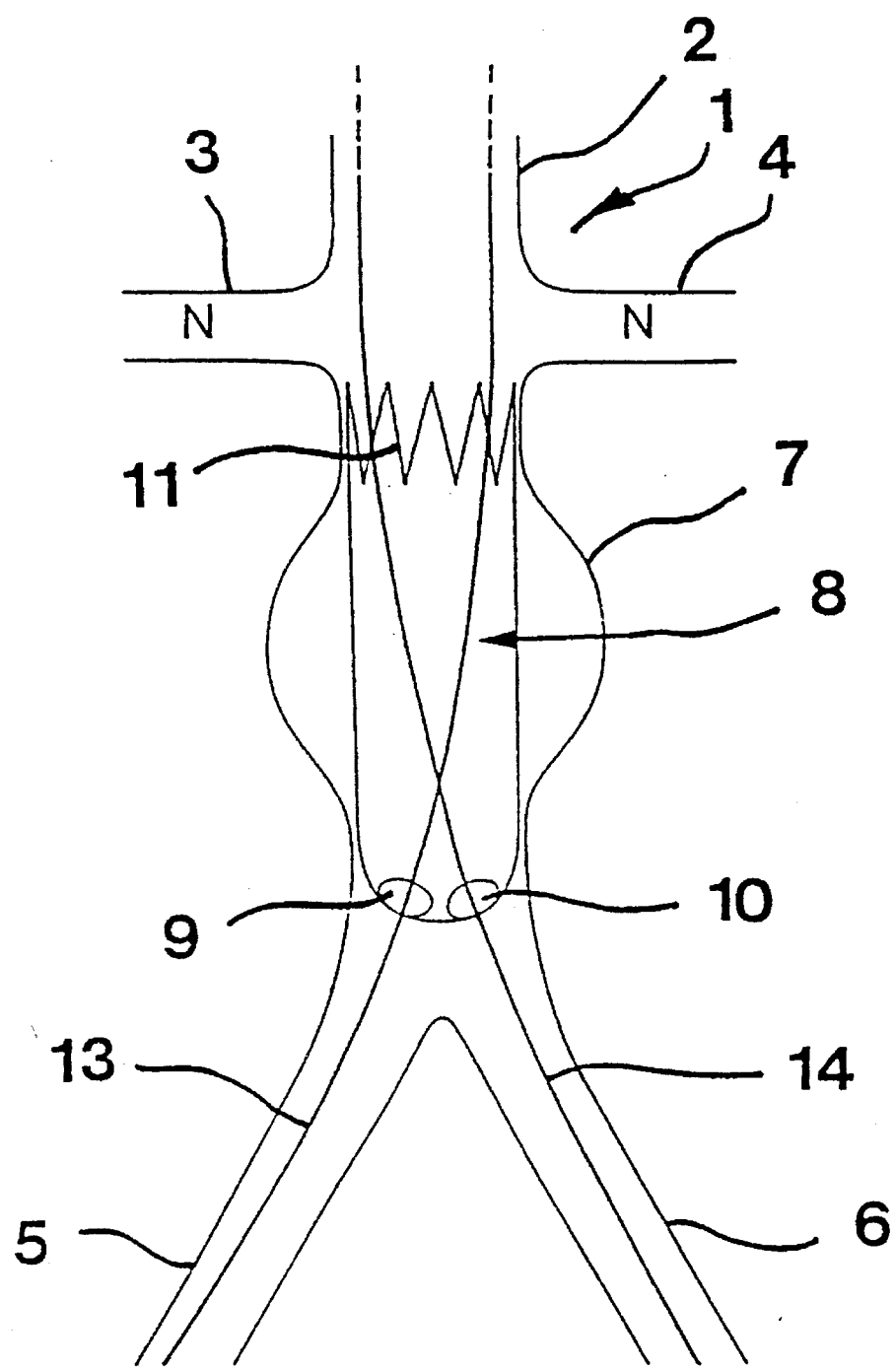

The invention will be further explained with reference to an embodiment shown on the schematical drawing in which FIG. 1 shows a bag-shaped main body of a prosthesis according to the invention deployed in expanded condition within an aortic aneurysm, FIG. 2 illustrates the introduction of two guide wires into the main body of FIG. 1 and FIG. 3 the main body completed with two leg stents into a prosthesis with a bifurcation.

Figure 3:
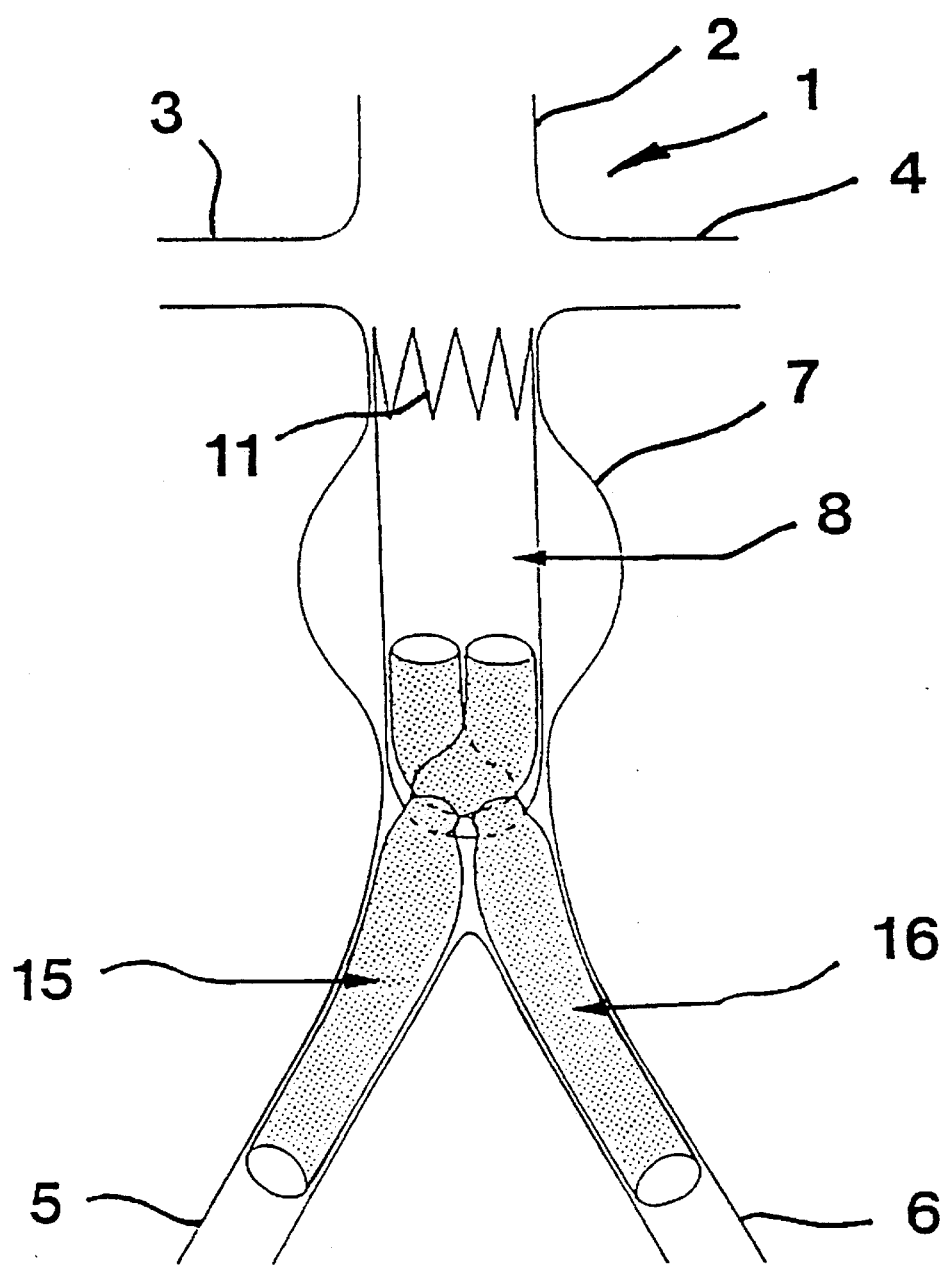

As example of the application of the invention, FIGS. 1 to 3 illustrate schematically an arterial system 1 in which the abdominal part of the aorta 2 extending between two branch arteries 3,4 leading to the kidneys and a bifurcation joining two iliac arteries 5,6 has been damaged by a balloon shaped aneurysm 7.

As illustrated in FIG. 1 a bag-shaped main body made of a micro-porous woven material unpenetratable to blood is first introduced in the region of the aneurysm 7 in the aorta 2, said main body being formed in a bottom region with two outlet openings 9,10. The main body 8 is provided with a self-expandable metallic stent 11 and is introduced in contracted condition through an iliac arteria 5 over a guide wire 12 and deployed in the aorta 2 in such a way that the metallic stent 11 will press at least the upper edge of the main body 8 tightly against the inner side of the aorta 2 above the aneurysm 7. In the bottom region of the main body 8 the guide wire 12 may as shown in dashed lines in FIG. 1 be bent so as to allow it to be guided outwards through the outlet opening and the other iliac arteria 6. Thereby a catheter not shown may be introduced over each of the free ends of the guide wire 12 until the main body 8 which has expanded due to the action of the blood flow. After removal of the guide wire 12 a single guide wire 13,14 may be introduced through each catheter to finalize the deployment preparation as illustrated in FIG. 2.

Over each of the guide wires 13,14 a self-expandable metallic stent 15,16 with an elastic covering may now be introduced in a conventional way. As illustrated in FIG. 3 a proximal end part of each of the metallic stents 15,16 projects into the interior of the main body whereas a distal end part of each metallic stent projects relatively deep into the iliac arteria 5,6.

In the expanded condition illustrated in FIG. 3 the metallic stents 15,16 are contracted in the rim region of each of outlet openings 9 and 10 and will thereby be firmly and tightly connected with the main body 8. Thereby, the main body together with the leg stents 15 and 16 will form an endovascular aortic prosthesis overlapping the aneurysm 7 and being implantable by relatively simple percutaneous operations.

We claim:

1. An endovascular graft prosthesis for arrangement at or in the vicinity of a bifurcation in the arterial system of a patient and comprising a substantially tubular main body for location in an upstream arteria above the bifurcation and substantially tubular legs joining said main body and adapted to extend via the bifurcation into each of two downstream branch arteries, said main body being made of a flexible microporous and surgically implantable woven material unpenetratable to blood, wherein the main body (8) is substantially bag-shaped with an open proximal upstream end having fixation means attached thereto and a distal downstream bottom region in which two outlet openings (9, 10) are provided, said main body being radially expandable and attachable in a radially expanded condition to the inner side of said upstream arteria (2) upstream of the bifurcation by said fixation means (11), said legs being separate resilient and radially expandable leg stent devices (15, 16) adapted for introduction in a collapsed condition through said branch arteries and into said outlet openings (9, 10) of said main body, each of said stent devices (15, 16) being engageable in its radially expanded condition against a rim of the corresponding outlet opening to provide a leakage-free bifurcated graft prosthesis.

2. An endovascular graft prosthesis as claimed in claim 1, wherein said fixation means comprises a main stent device (11) and is attached to the bag-shaped main body (8) with a downstream distal end of the main stent device (11) overlapped by the upstream proximal end of the main body (8).

3. An endovascular graft prosthesis as claimed in claim 2, wherein said main stent device (11) and leg stent devices (15, 16) include expandable metal stents.

4. An endovascular graft prosthesis as claimed in claim 3, wherein each outlet opening (9, 10) is positioned in the downstream direction.

5. An endovascular graft prosthesis as claimed in claim 4, wherein the maximum external diameter of each of the leg stent devices (15, 16) is 2–4 mm greater than the minimum rim diameter of each outlet opening (9, 10).

6. An endovascular graft prosthesis as claimed in claim 2, wherein each outlet opening (9, 10) is positioned in the downstream direction.

7. An endovascular graft prosthesis as claimed in claim 6, wherein the maximum external diameter of each of the leg stent devices (15, 16) is 2–4 mm greater than the minimum rim diameter of each outlet opening (9, 10).

8. An endovascular graft prosthesis as claimed in claim 1, wherein each outlet opening (9, 10) is positioned in the downstream direction.

9. An endovascular graft prosthesis as claimed in claim 8, wherein the maximum external diameter of each of the leg stent devices (15, 16) is 2–4 mm greater than the minimum rim diameter of each outlet opening (9, 10).

10. A method for implanting an endovascular graft prosthesis at or in the vicinity of a bifurcation in the arterial system of a patient and associated branch arteries, comprising the steps of:

introducing through a first branch arteria (5) in an upstream direction via a first guide wire (12) a separate, radially expandable and substantially bag shaped main body (8) into an upstream arteria to extend into a region thereof above the bifurcation, said main body having an open proximal upstream end with associated fixation means and a distal downstream bottom region in which two outlet openings (9, 10) are provided;

expanding said main body radially in said upstream arteria such that said proximal end becomes attached to the wall thereof; and introducing via other wires (12, 13, or 14) a radially expandable leg stent device (15, 16) through each of the branch arteries (5, 6) into each of said outlet openings.

11. An implantation method as claimed in claim 10, further comprising introducing a catheter through each of the branch arteries over each end of said first guide wire prior to the removal thereof, said catheters being subsequently used for introduction of said other guide wires.

* * * * *